United States Patent [19]

Inbar et al.

[11] Patent Number: 4,864,594
[45] Date of Patent: Sep. 5, 1989

[54] BONE MINERAL DENSITY MEASUREMENT

[75] Inventors: Dan Inbar, Haifa, Israel; F. Avraham Dilmanian, Shirley, N.Y.; Gideon Berlad, Haifa, Israel

[73] Assignee: Elscint Ltd., Haifa, Israel

[21] Appl. No.: 78,896

[22] Filed: Jul. 29, 1987

[30] Foreign Application Priority Data

Aug. 15, 1986 [IL] Israel .................................. 79733

[51] Int. Cl.$^4$ ..................... G01T 1/164; G01N 23/20
[52] U.S. Cl. ........................................ 378/5; 378/4; 378/19; 378/55; 250/363.01
[58] Field of Search ................... 378/5, 6, 11, 4, 53, 378/19, 16, 15, 54, 55; 250/363 R, 363 SH

[56] References Cited

U.S. PATENT DOCUMENTS

| | | |
|---|---|---|
| 3,715,558 | 2/1973 | McGill . |
| 3,848,130 | 11/1974 | Macovski .................. 378/53 |
| 3,996,471 | 12/1976 | Fletcher et al. . |
| 4,118,632 | 10/1978 | Luig ........................... 250/363 SH |
| 4,123,654 | 10/1978 | Reiss et al. ................. 378/5 |
| 4,547,893 | 10/1985 | Gordon ....................... 378/4 |
| 4,645,933 | 2/1987 | Gambini et al. ............ 250/363 SC |

OTHER PUBLICATIONS

Raikar et al., "Determination of Mineral Content in Bone by Photo Transmission Using Scintillation Camera", Int. J. Nuc. Meas. & Biol. (GB), 2(4), Oct. 1975, pp. 178-180.
Levy, Hoory, and Bandypadhyay, Estimation of Bone Mineral Content Using Gamma Camera: A Real Possibility, The Journal of Medicine, No. 88, 6/85, p. 24.
The book, by Wahner, H. W. et al., is entitled "Nuclear Medicine: Quantitative Procedures" published by Little Brown and Company, Toronto, Canada (1983).
"Assessment of Bone Mineral, Part 1", Journal of Nuclear Medicine by Wahner, H. W. et al., vol. 25, pp. 1134-1141 (1984).
"Bone Mineral Density of the Radius: Where Do We Stand?", Editorial in the Journal of Nuclear Medicine, pp. 1339-1341, 44, 45, vol. 26, No. 11 (1985).
"Assessment of Bone Mineral, Part 2", by Wahner, H. W. et al., Journal of Nuclear Medicine, vol. 25, No. 11, pp. 1241-1253 (1984).
"Quality Assurance of Gamma Camera as an Imaging System for Bone Mineral Content Evaluation", Abstract by Hoory, S. et al. in Radiology, vol. 157 (p), p. 87 (1985).
"A Dual Energy Photo Absorbtion Technique for Measurement of Bone Mineralization of the Spine Using a Gamma Camera", abstract by Wilson, C. R. et al., Radiology, vol. 157 (p), p. 88, (1985).

*Primary Examiner*—Carolyn E. Fields
*Assistant Examiner*—Joseph A. Hynds
*Attorney, Agent, or Firm*—Sandler & Greenblum

[57] ABSTRACT

In-vivo bone density measuring system using a modified emission computed tomographic gamma camera arrangement for detecting radiation from two separate sources located outside of the body of the patient and oppositely disposed to the gamma camera during rotation of the gamma camera and sources means about the patient for obtaining tomographic data. The two separate sources emitting at least two energy levels. The system includes processing means for the detected radiation to provide a bone mineral density map.

24 Claims, 2 Drawing Sheets

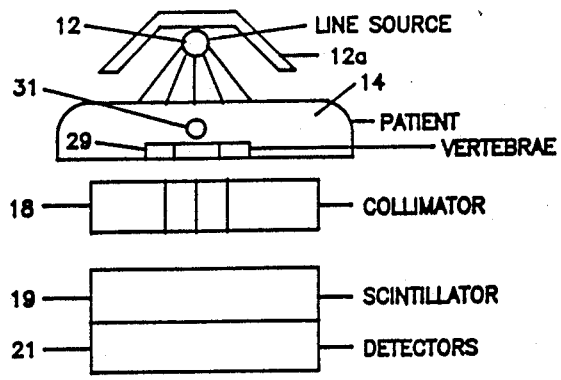
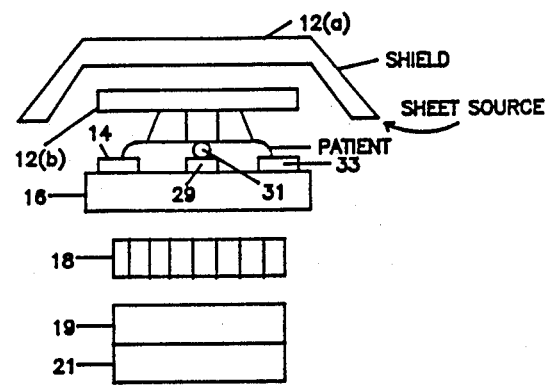
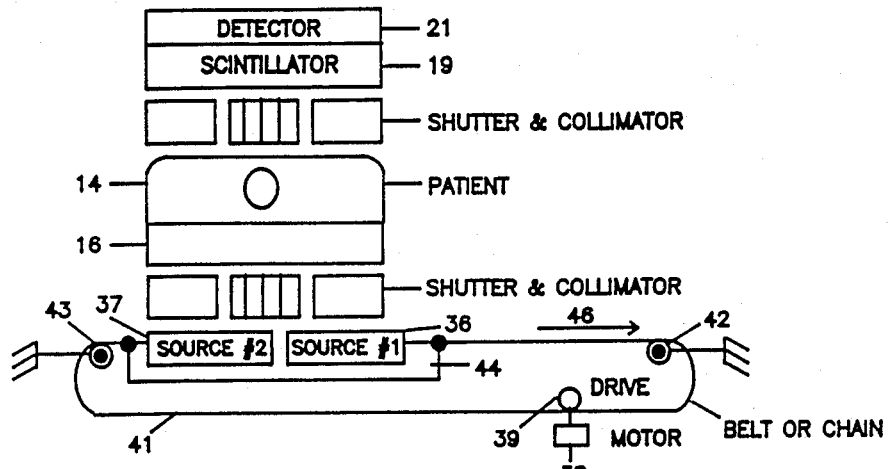

BONE MINERAL DENSITY MEASUREMENT

FIELD OF THE INVENTION

This invention is concerned with planar or tomographical mapping of the mineral content of bones for use, among other things, in monitoring bone mineral loss in adults, especially in woman after menopause, and for determining the effects of therapy used to counter bone loss from diseases such as osteoporosis. More particularly this invention is concerned with improved in-vivo bone mineral density measurements using gamma cameras in dual photon absorptiometry.

BACKGROUND OF THE INVENTION

There is an increasing interest in bone loss that occurs due to age, osteoporosis, or metabolic bone diseases. The impact of osteoporotic fractures on health care resources is significant at the present and is expected to increase even further. The necessity for being able to diagnose bone mineral content is accentuated by the therapeutic efforts made to restore or at least decelerate bone loss.

In the prior art, bone mineral content measurement techniques have included using radiographic methods, computerized tomographic methods, neutron activation analysis methods, single and dual photon absorptiometry methods and Compton absorptiometry methods. Recently, gamma cameras have been used for planar imaging in dual photon absorptiometry with a point source and a converging collimator.

For bone mineral mapping of the vertabrae and pelvic bones, which account for the largest number of fractures in adults, the most accurate methods are CT and dual photon absorptiometry. Use of single photon absorptiometry is practically limited to the forearm or humerus, femur or tibia, where the organ can be placed in a box filled with tissue equivalent material in order to limit the number of unknown parameters in the absorption equations to the bone mineral content only. Nevertheless, the accuracy of the single-photon measurement is still inferior and its clinical use is also questionable; since, there is little correlation between bone loss in the appendicular and the axial skeleton.

There is now available literature describing various bone mineral content mapping techniques and their limitations. See for example, "Nuclear Medicine: "Quantitative Procedures". by Wahner H W, Dunn W L, Thorsen H C, et al, published by Toronto Little, Brown & Co., 1983, (see pages 107-132). An article entitled "Assessment of Bone Mineral Part 1", appeared in the Journal of Nuclear Medicine, pp 1134-1141, (1984). Another article entitled "Bone Mineral Density of The Radius" appeared in Vol. 26, No. 11, (1985) Nov. Journal of Nuclear Medicine at pp 13-39. Abstracts on the use of gamma cameras for bone mineral content measurements are (a) S. Hoory et al, Radiology, Vol. 157(P), p. 87 (1985), and (b) C. R. Wilson et al, Radiology, Vol. 157(P), p. 88 (1985).

A prior art patent teaching a system for single photon absorptiometry is entitled "Bone Mineral Analyzer" and issued on Feb. 6, 1973 as U.S. Pat. No. 3,715,558. Another patent teaching a system for dual photon absorptiometry and indicative of the prior art is U.S. Pat. No. 3,996,471, entitled "Method and System for In-Vivo Measurement of Bone Tissue Using a Two Level Energy Source".

Many problems are encountered in the use of dual photon absorptiometry with a single detector. For example, it requires motion of the detector and the source in a very precise geometry; also, it is wasteful in terms of radiation dose to the patient, and time consuming in terms of locating the exact region of the bone.

The use of gamma cameras with point sources in planar dual photon absorptiometry solves the problems mentioned above. A remaining problem, however, is that the gamma rays impinge the body at a variety of angles. This means a two directional dispersion of the pathways of the gamma rays through the bones.

The dual photon absorptiometry measurements appearing in the literature primarily use the 153Gd isotope as a source of two gamma lines of 47 and 100 keV, with a fixed ratio of intensities of these two lines. Since the absorption of the lower line in the body is much stronger, the gamma detector sees a very large number of the high energy gamma rays compared to the low energy ones. In order to optimize the statistical accuracy of the measurement for a given total number of gamma rays of the given energies, a certain ratio of the intensities is required, not necessarily that dictated by the isotope.

The planar dual photon absorptiometry imaging with a single detector or with a gamma camera both have the handicap of measuring the collapsed projection of the body on the detector. This means that in cases where there are two layers of minerals over each other at the same position (e.g. The aorta calcification and the lumbar vertabrae), the measurements can not separate one from the other. Similarly, a planar image of the bone provides no information about its morphology, and therefore the planar images of cortical and trabecular bones are not separated. In particular, information as to whether bone loss occurs on the endosteal or periosteal bone envelope cannot be obtained.

BRIEF DESCRIPTION OF THE INVENTION

Accordingly, it is an object of the present invention to provide a dual photon absorptiometry system for bone mineral density mapping, said system comprising:

radiation source means of at least one dimension, emitting two gamma ray energies of substantially different ratios of absorption in soft tissue and in bone, a gamma camera for detecting the radiation from the radiation source means traversing a selected skeletal section in a patient, and for processing said detected radiation for the two said different energies to provide images for the two energies and a mineral bone density map, a mechanical system to position the radiation source means on one side of the said patient and the said gamma camera on the other side of said patient, collimator means to reduce the Compton scatter of the said gamma radiation reaching the said gamma camera, and a shutter to limit the radiation exposure only to a certain region of the body of the said patient including said selected skeletal section, A feature of the invention includes a system for in-vivo measurements of the density of bones of a patient to aid in determining the mineral content of the bones, the system comprising:

a gamma camera for detecting and locating the detected gamma radiation absorbed by the bones, means for positioning the gamma camera on one side of said patient, a point source of gamma radiation positioned on the other side of the patient whereby the gamma radiation from said source traverses the patient in transit to said gamma camera, means for obtaining image data of a desired skeletal section with said source and said camera, means for moving the point source in a single direction along a source collimator, said collimator being a slit collimator with the slit aligned perpendicular to the desired skeletal section, and a fan beam camera collimator with the axis along the bone and the line of focus on the source.

A further feature of the invention uses a line source of radiation at said source means of at least one dimension to limit errors caused by radiation paths of different lengths only to the direction transverse to the skeletal axis.

Yet another feature of the invention comprises using a sheet source of radiation as said source means of at least one dimension to further minimize errors caused by radiation path length variations.

Still another feature of the invention comprises a system having the capability of revolving both the source and the detector about the patient to provide tomographical images of slices through the patient. The tomographical images enable separating the mineral content determination of different layers of minerals that are superimposed in the planar images.

A related feature of the invention comprises modifying a standard emission computed tomographic (ECT) system to revolve both the source and the detector about the patient.

Yet another feature of the invention comprises preventing energy level contamination by separately applying the radiation emanating from individual energy sources.

A related feature of the invention comprises interlacing said two separate energy sources on a time basis to minimize errors caused by time dependent changes.

Still another related feature of the invention comprises applying the higher energy radiation for a shorter time period to minimize the time used for acquiring the data and thereby to increase throughput.

BRIEF DESCRIPTION OF THE DRAWING

The above mentioned and other features and objects of the present invention will be best understood when considered in the light of the following description of a broad aspect of the present invention as described hereinafter in conjunction with the accompanying drawings; in which:

FIG. 3 is an axial view of a line source such as may be used in FIG. 2;

FIG. 4 is an axial view of a sheet source of gamma ray radiation such as may be used in FIG. 2; and FIG. 5 is a schematic showing of a source selector arrangement for use in the inventive system of FIG. 1.

GENERAL DESCRIPTION

Figure 1:
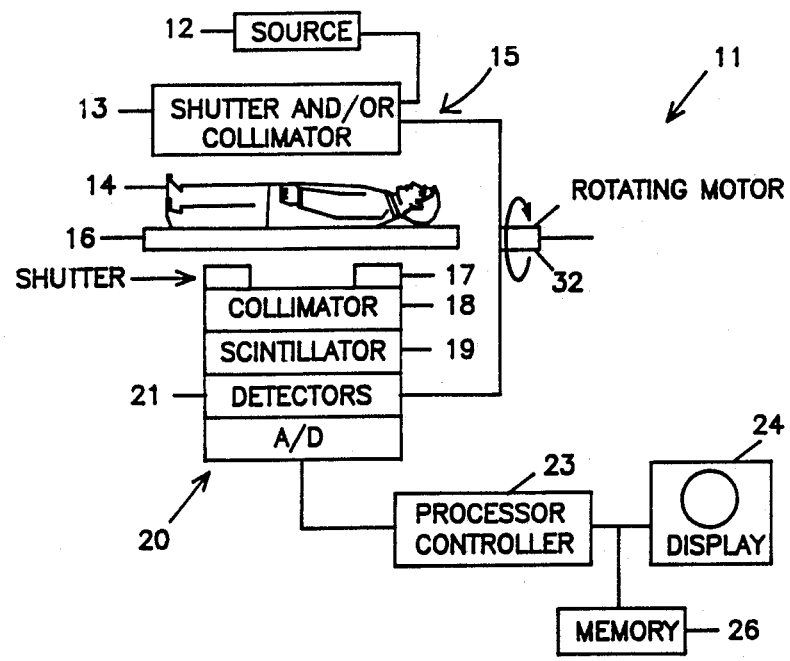
FIG. 1 is a block diagram showing of a bone mineral density measurement system using gamma cameras and showing improvements over present bone mineral density measurement systems which also use gamma cameras.

A bone mineral density measurement system 11 is shown in block diagram form in FIG. 1. The system 11 comprises a source 12 of at least one dimensional radiation. The term one dimensional for purposes of this description indicates that a point source is not used without movement. In other words, the source has at least a linear dimension; thus, if a point source is used it is moved at least linearaly. The source 12 may work in conjunction with a shutter and/or collimator 13. The source 12 provides gamma radiation which is directed towards a patient 14 by the shutter and/or collimator arrangement 13. After passing through the patient 14 and more particularly through selected skeletal sections of bones of the patient, including a single bone, the gamma radiation passes through a shutter arrangement 17 and a collimator 18. The collimator 18 is to assure that only direct radiation from the source and not Compton scatter or background radiation is measured.

The radiation after passing through the collimator 18 strikes a scintillator 19. The scintillator 19 operating responsive to impingement by photons of gamma radiation emits flashes of light which are detected by the photon detector means 21 (herein also sometimes referred to as "detector") and therein converted into electrical signals. The electrical signals are generally in analog form and are converted to digital form by analog-to-digital converter means 22. The conversion is usually done after calculation of the total pulse height and the coordinates x and y of the gamma event. The A/D converter or circuitry associated with the front end may include other functions, such as a threshold function and the like which are well known in the gamma camera art.

A processor controller 23 controls the operation of the system and processes the data for the display purposes. The display is shown as display 24. A memory 26 may be used in conjunction with the image processing and/or data processing.

The patient 14 is shown resting on a table 16. The source and collimator may be rotated about the patient to provide emission computer tomography type image data. The actual images may not be necessary, however they are extremely helpful in properly locating the patient relative to the system to assure that the desired skeletal sections or bones are being measured for bone mineral density. Thus certain of the spinal bones may be desired and/or certain sections of the hip bones may also be desired for the bone density measurement. With the described inventive arrangement, measurements can be made simultaneously on the pelvis and spinal column or on selected vertebrae and on selected portions of the pelvis. It is important to have correct measurements of the pelvic sections and vertebrae since the majority of breaks occurring due to osteoporosis occur in the pelvis section and in vertebrae.

As mentioned hereinbefore gamma cameras have been used heretofore for bone mineral density measurements and even for bone mineral measurements using dual energy sources. However, in the prior art, the gamma radiation sources have been point sources. The problem with point sources is that there are inaccuracies in the data acquisition because among other things the radiation from the source to the detector travels over paths of different lengths through the patient's bones. The radiation travels in a straight line normal to the patient or to the bones under examination only directly under the point source.

To prevent the data acquisition errors caused by the paths of different lengths and by the impingement of the body by gamma rays at a variety of angles and the consequent two directional dispersion of the gamma rays through the bones, a radiation source of at least one dimension is used in conjunction with the gamma ray camera equipment in the inventive bone mineral density measurement system 11. Point sources may be used within the scope of the invention, if the point source is moved or effectively moved along for example the vertebrae to enable the gamma radiation to strike each of the disks of the vertebrae being examined at a 90 degree angle; i.e., be perpendicular to the vertebrae being examined along the line of movement of the point source. Thus in effect a linear source is provided which is a source having at least one dimension.

Figure 2:
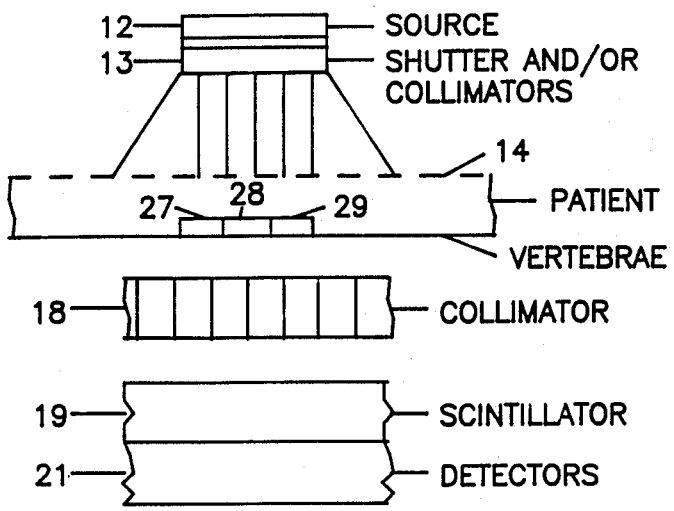
FIG. 2 is a detailed block diagram showing of a line or point source of gamma radiation used in conjunction with this invention.

FIG. 2 shows the source 12 and shutters and/or collimators 13 in a side view. Also shown are three vertebrae 27-29 of the spinal column of patient 14, which are being examined to determine their mineral density. As shown in FIG. 2, the collimator 18 works in conjunction with the scintillator 19 and the detectors 21 to limit the radiation striking the scintillator to radiation that is normal to the central axis of the vertebrae 27, 28 and 29 as the radiation passes through the patient 14 in transit to the gamma camera equipment.

An axial view of the arrangement of FIGS. 1 and 2 is shown in FIG. 3. Therein, the source is shown as line source 12 in a source holder 12a which also acts as a partial shutter and/or collimator. In the axial view it is seen that the line source because of its position directly above and parallel to the vertebrae does transmit a large percentage of its radiation in a direction normal to the central axis of the vertebrae. The collimator 18 is shaped so as to eliminate Compton scatter in the direction transverse to the axial direction as well as in the direction transverse to the longitudinal direction shown in FIG. 2. Thus, the scintillator receives gamma radiation photons that are perpendicular to the vertebrae and thus, have a practically constant path length through the patient 14 and through the vertebrae 27-29 of the patient.

In FIG. 4, which is also an axial view of FIG. 2, the source is shown as a sheet source 12b. Here the shield or holder 12a is shaped to retain the sheet source. The sheet source enables supplying radiation through the patient 14 on table 16, which is directed perpendicular to both vertebrae and the pelvic bones. This enables obtaining data on the vertebrae and the pelvis simultaneously.

When examining certain parts of the body, overlapping organs or bodyparts having high mineral content cause confusing results in a planar x-ray view. For example, the aorta shown as 31 in FIG. 4 is aligned with the spinal column as indicated such as by the showing of vertebra 29 under aorta 31. To overcome this problem an ECT arrangement is used. The ECT arrangement as shown in FIG. 1 include a motor 32 which rotates both the source equipment 15 and the gamma camera equipment, generally shown as 20. The source equipment includes the source and/or collimator arrangements along with a source holding shield. The gamma camera detecting equipment 20 includes a collimator, a scintillator, photon detectors and "front end" electronics along with any shutter arrangement that may be used.

The ECT arrangement particularly enables distinguishing the mineral content of the aorta 31, for example, from the mineral content of the bones. Thus in a prior art planar image of vertebrae it is difficult if not impossible to distinguish the mineral content of the aorta and the mineral content of vertebrae. Accordingly, the aorta which has a high mineral content distorts the measurement of the mineral content of the vertebrae. The tomographic image provided by the ECT equipment overcomes this problem.

In the inventive system as has been done in the past, bone and tissue are distinguished by using a high energy source and a low energy source. The use of two energy sources for distinguishing between tissue and bone is well known. The present improvement over the prior art systems lies, for example, in using a system such as shown in FIG. 5. Therein instead of a single energy source that radiates two different energy levels, two separate energy sources are used. For example, the high energy source which transmits many more gamma photons per time period than a low energy source, can thus be kept in a position irradiating the patient for a shorter time period than the low energy source which emits fewer photons per time period. The two separate energy sources speed up the throughput time of the system. Thus, where a single energy source with two gamma levels, such as 153Gd is utilized, then the time that the energy source must be maintained over the patient is determined by the lower energy source. The feature of utilizing two separate energy sources also prevents energy level contamination.

There is of course a certain amount of overlapping in the measured radiation outputs of the two energy sources because of Comptons scattering of the high energy line. Thus, using two different sources eliminates confusion regarding the source of the radiation. Also, when the two energy sources are interlaced then errors caused by time dependent changes are minimized.

The system in FIG. 5 includes the two energy sources shown as source 36 and 37. A drive motor 38 moves the energy sources under the collimator and away from a position under the shutter as desired. The driver motor rotates a drive wheel 39 which moves a belt or chain 41 directed through pulleys, such as pulleys 42 and 43 to move the source container 44 to the right or the left as shown by arrow 46. The sources may be interlaced as mentioned and maintained under the collimator and out from behind the shutter for determined periods of time to most effectively irradiate the patient and eliminate errors due to patient's involuntary motions, such as motions caused by breathing for example.

The invention has been explained in relation to some preferred embodiments. It must be understood that the embodiments are described by way of example only and not as limitations on the scope of the invention.

What is claimed is:

1. A system for in-vivo measurements of mineral density of bones of a patient, such system comprising:
    radiation source means of at least one dimension, said source means emitting gamma radiation of at least two different energy levels,
    a gamma camera for detecting the gamma radiation from the radiation source means traversing a selected skeletal section in the patient,
    means for processing the detected gamma radiation of the at least two said energy levels to provide a mineral bone density map, apparatus to position the radiation source means on one side patient and said gamma camera on the other side of said patient, said apparatus to position the radiation source means on one side of said patient and said gamma camera on other side of said patient further comprising means for rotating said radiation source means and said gamma camera around the patient to obtain tomographic data from said detected radiation, collimator means to reduce Compton scatter of the said gamma radiation and to minimize background radiation reaching said gamma camera, and a shutter to enable exposing only certain regions of the body of said patient including said selected skeletal section to gamma radiation from said radiation source means.

2. The system of claim 1, wherein said source means comprises a line source means.

3. The system of claim 1 wherein said source means comprises a sheet source means.

4. The system of claim 3 wherein said collimator means is a slit collimator having a slit aligned parallel to an axis of said selected skeletal section so that the radiation is perpendicular to the axis of said selected skeletal section 5. The system of claim 3 wherein said collimator means includes a fan-beam collimator with a slit of the collimator being parallel to a bone of said selected skeletal section and a line of focus of said fan-beam camera collimator being at the source means.

6. A system for in-vivo measurements of mineral density of a bone of a patient, said system comprising:

radiation source means of at least one dimension, said radiation source means comprising a first and a second individual energy sources, said first individual energy source having a higher energy than the second individual energy source, a gamma camera for detecting the gamma radiation from said radiation source means traversing a selected skeletal section in a patient, means for processing the detected gamma radiation from said first and second individual energy sources to provide a bone mineral density map, apparatus to position the radiation source means on one side of said patient and said gamma camera on the other side of said patient, said apparatus to position the radiation source means on one side of said patient and said gamma camera on other side of said patient further comprising means for simultaneously rotating said radiation source means and said gamma camera around the patient to obtain tomographic data from said detected radiation, collimator means to reduce Compton scatter and to minimize background radiation reaching said gamma camera, and a shutter to enable exposing certain regions of the body of said patient including said selected skeletal section to gamma radiation from said radiation source means.

7. The system of claim 6 including means for interlacing said first and second individual energy sources on a time basis to minimize errors caused by time dependent changes.

8. The system of claim 7 wherein means are provided for applying the first individual energy source for a short time period then the second individual energy source to minimize the time used for acquiring data so as to increase throughput.

9. The system of claim 8 wherein a positioning means for individually positioning the first and second individual energy sources to individually radiate the patient is provided, said positioning means positioning said first individual energy sources juxtaposed to a collimator while the second individual energy source is positioned juxtaposed to a shutter to prevent the radiation from said second individual energy source from reaching the patient while the radiation from the first individual energy source is applied to the patient, and means for measuring the time each of said individual energy source radiates a patient.

10. The system of claim 9 including means for maintaining said first individual energy source juxtaposed to a collimator for a first time period and means for interchanging said first and second energy sources for a second time period.

11. The system of claim 10 wherein said collimator is a slit collimator having a slit aligned parallel to the selected skeletal section.

12. The system of claim 10 wherein said collimator means is a fan-beam collimator having an axis along the selected skeletal section and having a line of focus at the source means.

13. A method for in-vivo measurements of mineral density of bones of a patient, said system comprising:

emitting gamma radiation of at least two different energy levels from radiation source means, detecting the emitted radiation traversing a selected skeletal section in the patient with a gamma camera, positioning the radiation source means on one side of said patient and said gamma camera oppositely disposed on the other side of said patient, rotating said radiation source means and said gamma camera about the patient to obtain tomographic data from said detected radiation, collimating said radiation to reduce Compton scatter of said gamma radiation reaching said gamma camera, exposing only certain regions of the body of said patient including said selected skeletal section to said gamma radiation, and processing said detected gamma radiation of the at least two said different energy levels to provide a mineral bone density map.

14. The method of claim 13 wherein said source means comprises a line source means.

15. The method of claim 13 wherein said source means comprises a sheet source means.

16. The method of claim 13 wherein said collimating step includes slit collimating along a slit aligned parallel to the selected skeletal section.

17. The method of claim 13 wherein said collimating step includes fan-beam collimating with a collimating slit along a bone of the selected skeletal section and a collimator line of focus being at the source means.

18. A method for in-vivo measurements of mineral density of bones of a patient, said method comprising:

emitting gamma radiation of at least two different energy levels from radiation source means, the emitting gamma radiation step including using at least a first individual energy source and a second individual energy source, said first individual energy source having a higher energy than the second individual energy source, detecting gamma radiation from said radiation source means traversing the skeletal section in a patient with a gamma camera, processing the detected gamma radiation of the said two different energy levels to provide a bone mineral density map, positioning the gamma radiation source means on one side of said patient and said gamma camera on the other side of said patient, rotating said radiation source means and said gamma camera about the patient to obtain tomographic data from said detected radiation, collimating said radiation to reduce Compton scatter of said gamma radiation reaching said gamma camera, and exposing only certain regions of the body of said patient including said selected skeletal section to said gamma radiation from said radiation source means.

19. The method of claim 18 including interlacing said two individual energy sources on a time basis to minimize errors caused by time dependent changes.

20. The method of claim 18 including applying the first individual energy source for a shorter period of time than the second individual energy source to minimize time used for acquiring data so as to increase throughput.

21. The method of claim 19 wherein said positioning step comprises:

individually positioning the first and second individual energy sources to individually radiate the patient, said individually positioning step including positioning said first individual energy source juxtaposed to a collimator while positioning the second individual energy source juxtaposed to a shutter to prevent radiation from said second individual energy source from reaching the patient while radiation from the first individual energy source is applied to the patient, interchanging said first and second individual energy sources, and measuring the time each individual energy source radiates a patient.

22. The method of claim 20 including maintaining said first individual energy source juxtaposed to the collimator for a first time period and said second individual energy source juxtaposed to the collimator for a second time period and interchanging the first and second individual energy sources for a second time period.

23. The method of claim 21 wherein said collimating step includes slit collimating with a slit aligned perpendicular to the selected skeletal section.

24. The method of claim 21 wherein said collimating step includes collimating with a fan-beam camera collimator with a slit aligned parallel to the selected skeletal section and a line of focus at the source means.

* * * * *